United States Patent
Davis et al.

(10) Patent No.: US 9,968,388 B2
(45) Date of Patent: May 15, 2018

(54) SURGICAL INJECTION SYSTEM AND METHOD

(71) Applicants: Darren L. Davis, Arlington, TN (US); Eric C. Lange, Collierville, TN (US)

(72) Inventors: Darren L. Davis, Arlington, TN (US); Eric C. Lange, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 523 days.

(21) Appl. No.: 14/667,383

(22) Filed: Mar. 24, 2015

(65) Prior Publication Data

US 2016/0278822 A1 Sep. 29, 2016

(51) Int. Cl.
| | |
|---|---|
| *A61M 29/00* | (2006.01) |
| *A61B 17/70* | (2006.01) |
| *A61F 2/46* | (2006.01) |
| *A61B 17/88* | (2006.01) |
| *A61M 5/36* | (2006.01) |
| *A61M 39/24* | (2006.01) |

(52) U.S. Cl.
CPC ...... *A61B 17/7097* (2013.01); *A61B 17/7061* (2013.01); *A61B 17/7065* (2013.01); *A61B 17/8841* (2013.01); *A61F 2/4611* (2013.01); *A61M 5/36* (2013.01); *A61M 2039/242* (2013.01)

(58) Field of Classification Search
CPC .... A61J 11/0005; A61F 2/44; A61B 17/7097; A61B 17/7061; A61B 17/7065
USPC ......................................................... 604/77
See application file for complete search history.

(56) References Cited

U.S. PATENT DOCUMENTS

| | | | |
|---|---|---|---|
| 7,001,431 B2* | 2/2006 | Bao ..................... | A61B 17/7097 606/247 |
| 2011/0015728 A1* | 1/2011 | Jimenez ............... | A61F 2/2418 623/2.11 |

* cited by examiner

*Primary Examiner* — Phillip Gray

(57) ABSTRACT

A surgical injection device comprises a longitudinal element. A first member is disposed with the longitudinal element and includes a mating surface. A second member is disposed with the longitudinal element and includes a mating surface engageable with the mating surface of the first member. A valve is disposed with the members and axially translatable relative to the members between a vent position and a seal position. Systems and methods are disclosed.

20 Claims, 3 Drawing Sheets

SURGICAL INJECTION SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes corpectomy, discectomy, decompression, fusion, fixation, laminectomy and implantable prosthetics. In some cases, surgical treatment can include introducing biomaterials to a surgical site for repairing and/or restoring a vertebra and/or an intervertebral disc. Spinal stabilization treatments may employ such biomaterials with implants, which may include interbody devices, plates and bone fasteners to stabilize vertebrae and facilitate healing. In procedures, such as, for example, corpectomy and other procedures for treating a vertebral compression fracture, biomaterial can be injected into a vertebra, directly or in some cases with a surgical balloon inserted into a vertebra, for expansion and/or to restore a collapsed vertebra to its original shape. In other procedures, such as, for example, discectomy, disc replacement and/or disc nucleus replacement, biomaterials can be injected into an intervertebral disc space to augment the procedure and restore intervertebral disc space height. This disclosure describes an improvement over these technologies.

SUMMARY

In one embodiment, a surgical injection device is provided. The surgical injection device comprises a longitudinal element. A first member is disposed with the longitudinal element and includes a mating surface. A second member is disposed with the longitudinal element and includes a mating surface engageable with the mating surface of the first member. A valve is disposed with the members and axially translatable relative to the members between a vent position and a seal position. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
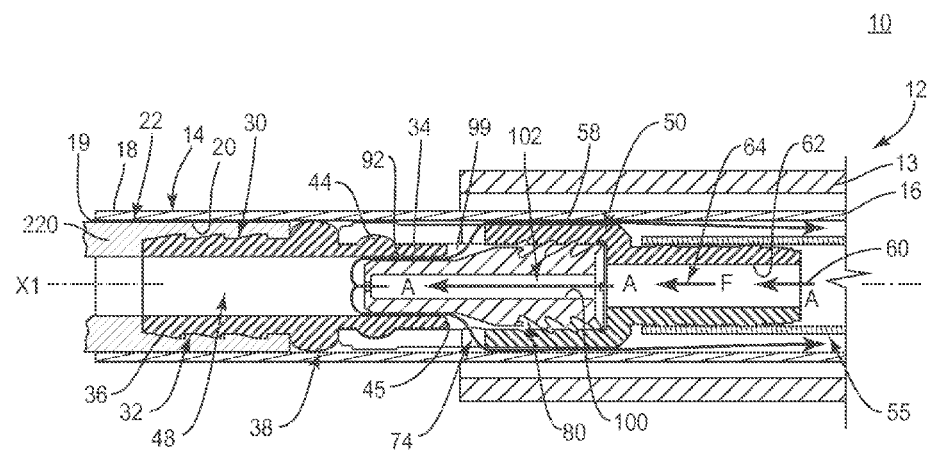
FIG. 1 is a break away cross section view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and a method for treating a spine.

In some embodiments, the surgical system includes a surgical instrument, such as, for example, a surgical injection device. In some embodiments, the surgical injection device is employed with an implant and/or expandable member that can be injected with a material such as a liquid and/or a slow moving solid into or to form in situ. In some embodiments, the surgical injection device injects a material into a balloon-type of expandable structure or a structure expanded by infusion of material.

In some embodiments, the surgical system includes a surgical injection device comprising a liquid/gas separator. In some embodiments, the surgical injection device is configured to allow air to vent from a tube prior to the injection of silicone into an implant. In some embodiments, the surgical injection device is employed with a minimally invasive surgical procedure. In some embodiments, the surgical injection device is configured to vent a gas and includes a check valve that shifts position when a viscous liquid moves through the surgical injection device. In some embodiments, this configuration creates a mechanical seal such that an implant connected with the surgical injection device can be pressurized and filled with such liquid. In some embodiments, the surgical injection device includes a locking feature and a liquid/gas check valve. In some embodiments, the surgical injection device is connected with an implant that is injected with a liquid and the surgical injection device is employed to remove air from the liquid and through the surgical injection device, for example, tubing of the surgical injection device, to resist and/or prevent the transfer of air into the implant.

In some embodiments, the surgical injection device comprises a gas/liquid separation device that allows an initial release and/or escape of a gas trapped within a transfer volume, which includes one or more liquids. In some embodiments, the surgical injection device includes an implant connector such that additional devices can be connected to the implant connector to provide for additional encapsulated transfer volume for injecting liquid into such devices.

In some embodiments, the surgical injection device comprises a first cannula, a second cannula, a third cannula, a male connector including a ring seal and an implant connector end, a female connector including a gas vent, a gas/liquid check valve and a transfer volume supplied via the third cannula. In some embodiments, the surgical injection device comprises mating internal and external locking features between the female and male connectors that resist and/or prevent pull forces to separate the connectors when circumferentially constrained. For example, the second cannula constrains the female connector from increasing in diameter, which mechanically locks the male and female connectors together. In some embodiments, after the transfer of a liquid is complete, the second cannula can be retracted to release the female connector and allow the male connector to disconnect with minimal pull force.

In some embodiments, the gas/liquid check valve is movable between two positions. In some embodiments, the gas/liquid check valve is disposable in a gas venting position. In some embodiments, the gas venting position is configured such that a gas travels through the third cannula and the check valve, and the gas exits through a tip of the check valve without shifting the valve. In some embodiments, this configuration allows the gas to vent around clearances between an outside surface of the check valve and the male connector. In some embodiments, this configuration allows the vented gas to follow a pathway around the check valve, through gas vents, and around a perimeter of the female connector. The vented gas exits between the passageway of the second cannula and the clearance of the third cannula.

In some embodiments, the gas/liquid check valve is disposable in a liquid constrained position. In some embodiments, the liquid constrained position is configured such that the gas/liquid check valve is shifted by the viscosity of the transfer liquid such that an outer taper of the check valve creates a mechanical seal on an inside edge and/or rim of the male connector. In some embodiments, an internal pressure within the third cannula, connectors, and an implant connected with the male connector forces the valve taper feature to be held under pressure against the male connector and provides a mechanical seal to restrict liquid transfer into the connected implant device only and not leak into the same pathway as the vented gas.

In some embodiments, the male connector includes an outside ring seal surface that creates a positive interference fit within the second cannula. This configuration creates two distinct portions of a passageway of the second cannula. In some embodiments, the implant connector end is joined with a constrained volume, such as, for example, an expandable member. As such, the transfer volume is restricted to conform within a portion of the passageway of the second cannula, the female and male connectors, the device and/or an expandable member attached to the implant connection end, and between the second cannula and the third cannula. In some embodiments, the ring seal surface on the outside surface of the male connector separates vented gas and substances outside of the attached devices from mixing.

In some embodiments, the female connector comprises one or more slots that allow circumferential expansion when not constrained, for example, by the second cannula. In some embodiments, the male connector includes an intimate mating feature that is inserted into a connecting groove of the female connector. In some embodiments, the male and female connectors are connected such that the female connector outer surfaces are not constrained.

In one embodiment, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
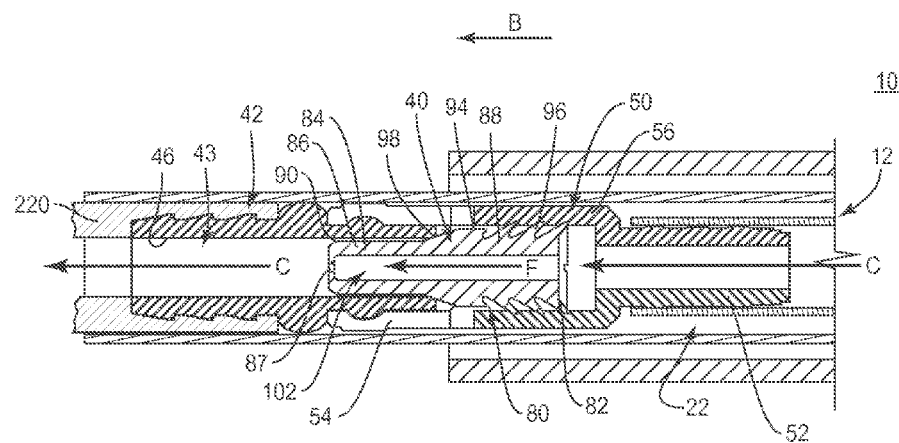
FIG. 2 is a break away cross section view of components of one embodiment of a surgical system in accordance with the principles of the present disclosure.
Figure 3:
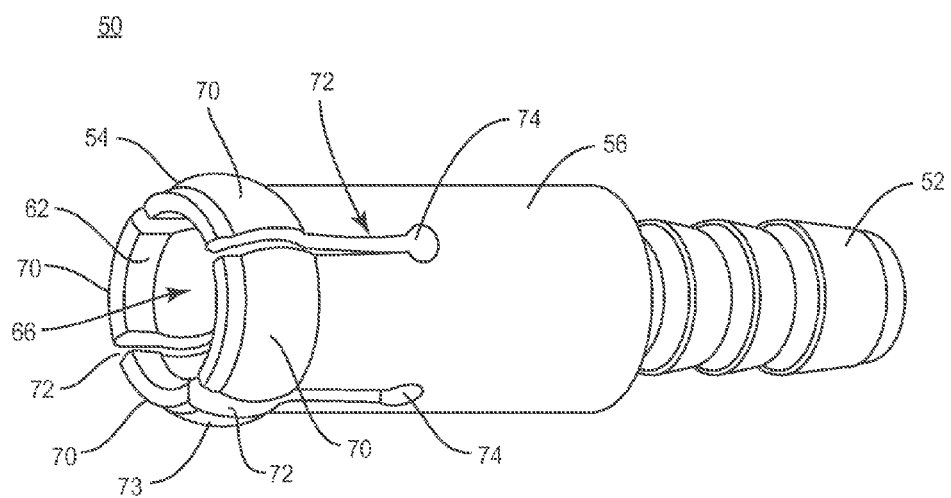
FIG. 3 is a perspective view of components of one embodiment of a surgical system in accordance with the principles of the present disclosure.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system 10 including a surgical instrument 12.

The components of surgical system 10 can be fabricated from biologically acceptable materials suitable for medical applications, including metals, synthetic polymers, ceramics and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical instrument 12 can be employed, for example, with percutaneous surgical implantation, minimally invasive surgery, mini-open and open surgical techniques to prepare a surgical site including tissue in connection with a surgical procedure, introduction of surgical instrumentation and/or delivery and introduction of one or more biomaterials and/or an implant, such as, for example, spinal implants, plates, an intervertebral implant, interbody devices and arthroplasty devices at a surgical site within a body of a patient, for example, a section of a spine. In one embodiment, surgical system 10 may be employed with surgical procedures, such as, for example, decompression, corpectomy and discectomy, which can include fusion and/or fixation treatments that employ implants.

The components of surgical system 10 can include, and/or surgical instrument 12 can be employed with, a longitudinal element, such as, for example, an outer cannula 13, which is configured to facilitate introduction and/or delivery of the components of surgical system 10 to a surgical site, as described herein, and/or engage tissue. In some embodiments, outer cannula 13 may include one or more needles, trocars, sheaths and/or minimally invasive instruments. In some embodiments, outer cannula 13 may include a cutting surface that can be extended and retracted to cut and/or sever tissue and/or components of surgical system 10. In some embodiments, outer cannula 13 may be guided via imaging guidance, as described herein.

Surgical instrument 12 includes a longitudinal element, such as, for example, a cannula 14. Cannula 14 extends between a proximal end 16 and a distal end 18, which defines an opening 19 configured for disposal adjacent a surgical site, as described herein. In some embodiments, opening 19 is configured to facilitate introduction and/or delivery of the components of surgical system 10 to a surgical site. Cannula 14 defines a longitudinal axis X1. In some embodiments, cannula 14 may have cross section configurations, such as, for example, oval, cylindrical, triangular, square, polygonal, irregular, uniform, non-uniform, offset, staggered, undulating, arcuate, variable and/or tapered.

Cannula 14 includes an inner surface 20 that defines an axial passageway 22 that extends along axis X1. Passageway 22 is configured for disposal of components of surgical system 10, as described herein. In some embodiments, passageway 22 may have cross section configurations, such as, for example, oval, cylindrical, triangular, square, polygonal, irregular, uniform, non-uniform, offset, staggered, undulating, arcuate, variable and/or tapered. In some embodiments, cannula 14 may be extended and/or retracted from cannula 13 for positioning adjacent a surgical site and/or delivering an implant to a surgical site. In some embodiments, cannula 14 may include a cutting surface that can be extended and/or retracted from cannula 13 to cut and/or sever tissue and/or components of surgical system 10. In some embodiments, cannula 14 may be guided via imaging guidance, as described herein.

Surgical instrument 12 includes a member, such as, for example, an implant connector 30. Connector 30 extends between an end 32 and an end 34. End 32 is disposed in passageway 22 adjacent opening 19 and is oriented to connect surgical instrument 12 with an expandable member, such as, for example, a spinal implant 220. End 32 is configured for engagement with a connector and/or a fluid port of a spinal implant, as described herein. In some embodiments, end 32 is connected with a spinal implant and configured for implantation with the spinal implant in a patient.

In some embodiments, the expandable member includes an implantable inflatable balloon, an implantable inflatable membrane or an implantable member having a fluid seal that is configured to expand with inflation by an injectable biomaterial and/or a pressurized expanding medium, as described herein. In some embodiments, the inflatable balloon defines a cavity, such as, for example, an inflatable chamber configured for receiving an injectable biomaterial and/or a pressurized expanding medium to expand the inflatable balloon to an expanded configuration. In some embodiments, the inflatable balloon may define one or a plurality of cavities configured for receiving an injectable biomaterial and/or a pressurized expanding medium, which may or may not be in communication and/or separately expandable. In some embodiments, the expandable member comprises an interspinous implant, as described herein. In some embodiments, the interspinous implant includes an H-shaped inflatable balloon configured for engagement with adjacent spinous process.

In some embodiments, the expandable member is inserted into cannula 14 and fixedly attached with connector 30 such that connector 30 remains in the patient after implant. In some embodiments, end 32 includes an outer surface 36 that comprises a connection device, such as, for example, a luer connection, a Tuohy-Borst connection or other suitable connection with the expandable member to facilitate transfer of an injectable biomaterial and/or a pressurized expanding medium, such as, for example, a fluid F into the expandable member, as described herein.

Connector 30 includes an inner surface 46. Surface 46 defines an axial passageway 48. Passageway 48 is in communication with passageway 22 to facilitate injection of fluid F into an expandable member, as described herein. Passageway 48 is configured for moveable disposal of a valve 80, as described herein. In some embodiments, passageway 48 may have cross section configurations, such as, for example, oval, cylindrical, triangular, square, polygonal, irregular, uniform, non-uniform, offset, staggered, undulating, arcuate, variable and/or tapered.

End 34 is configured to mate with a member, such as, for example, a vent connector 50, as described herein. Surface 36 includes a seal, such as, for example, a flange 38 circumferentially disposed about connector 30. Flange 38 is configured to engage surface 20 to create a mechanical seal therewith. As such, the flange 38/surface 20 engagement forms a fluid barrier between selected portions of passageway 22 to facilitate flow of fluid F to an expandable member.

Surface 36 includes a mating surface, such as, for example, a circumferential band 44. Band 44 is configured to mate with connector 50, as described herein. Band 44 engages a mating surface of connector 50 to interlock connectors 30, 50 in a fixed engagement within cannula 14. As such, valve 80 is movable relative to connectors 30, 50 between a vent position and a seal position, as described herein. Connector 30 includes an end surface 45 configured for engagement with a surface of valve 80 to create a mechanical seal therewith, as described herein. Engagement of end surface 45 and valve 80 facilitates transfer of fluid F to an expandable member.

Surgical instrument 12 includes connector 50 that is configured for disposal in passageway 22. Connector 50 extends between an end 52 and an end 54. End 52 is configured for connection with a source 55 of an injectable biomaterial and/or a pressurized expanding medium, such as, for example, fluid F for transfer into an expandable member, as described herein. In some embodiments, end 52 is attached with source 55 via a connection device, such as, for example, a luer connection or a Tuohy-Borst connection or other suitable connection device, which may include cannulae and/or tubing to facilitate transfer of fluid F into an expandable member.

In some embodiments, end 52 is connected to a source of fluid F, such as, for example, silicone, injectable polymer, sterile water, saline, inflating air and/or other fluids and gases, and/or combinations thereof. In some embodiments, fluid F is introduced into an expandable member via the components of surgical instrument 12 at a pressure in a range of 3 pounds per square inch (psi) to 5000 psi. In some embodiments, fluid F may be introduced into an expandable member via the components of surgical instrument 12 at constant or varied pressure, and/or can be measured by a gauge. In some embodiments, a source of fluid F may be a syringe barrel with plunger, pressurized container and/or wall connection. In some embodiments, the flow of fluid F and/or the pressure of fluid F being introduced into an expandable member may be regulated and/or valve controlled manually, electronically or processor controlled. In some embodiments, fluid F can be introduced into an expandable member via a single fluid and/or gas source with a manifold and independently controlled valves.

Connector 50 includes an inner surface 62 that defines an axial passageway 64. In some embodiments, passageway 64 may have cross section configurations, such as, for example, oval, cylindrical, triangular, square, polygonal, irregular, uniform, non-uniform, offset, staggered, undulating, arcuate, variable and/or tapered. Passageway 64 is in communication with passageways 22, 48 and valve 80 to facilitate flow of fluid F into an expandable member. Connector 50 includes an outer surface 56. Upon disposal of a connector 30/50 assembly within cannula 14 and in engagement with surface 20, surface 56 is spaced apart from surface 20 to define a clearance 58. Clearance 58 defines a portion of a vent pathway 60, as described herein.

Surface 62 includes a mating surface, such as, for example, a circumferential recess 66 disposed at end 54. Connector 50 includes a plurality of movable arms 70. Arms 70 are circumferentially disposed about end 54 and extend in a cantilevered configuration from connector 50. Each arm 70 defines a portion of recess 66 and includes an enlarged outer surface 73. Arms 70 define slots 72 therebetween. Slots 72 are disposed axially between arms 70 and extend between outer surface 56 and surface 62. Slots 72 each include a lateral opening, such as, for example, a vent opening 74. Slots 72 facilitate expansion and contraction of arms 70, as described herein.

Connector 30 is engageable with connector 50 between a locked position, as shown in FIGS. 1 and 2, and a release position, as shown in FIG. 3. To dispose connector 50 in the locked position, end 34 is disposed within passageway 64 and band 44 is aligned with recess 66. The assembly of connectors 30, 50 is inserted and translated within passageway 22 such that surfaces 73 engage surface 20. Arms 70 are forced inward so that end 34 engages end 54. Recess 66 receives and mates with band 44 in a fixed engagement to interlock connectors 30, 50. End 54 mates with end 34 to interlock connectors 30, 50 in a fixed engagement within cannula 14 such that valve 80 is movable relative to connectors 30, 50 between a vent position and a seal position, as described herein.

From the locked position, arms 70 are resiliently biased outward. The assembly of connectors 30, 50 is translated from passageway 22 and removed from cannula 14 such that surfaces 73 disengage from surface 20. Arms 70 deflect outward to release band 44 from recess 66. Connector 30 is releasable from connector 50. In some embodiments, the assembly of connectors 30, 50 is removed from cannula 14 and connector 30 is releasable from connector 50 in a quick-release configuration.

Valve 80 extends between an end 82 and an end 84. Valve 80 is configured to regulate the flow of fluid F, as will be described. In some embodiments, valve 80 may provide a continuous or regulated flow of fluid F, and/or may be electronically or processor controlled. In some embodiments, valve 80 may be tapered or include a cap or clip structure for preventing flow. In some embodiments, valve 80 may include a luer lock, and/or attachment with a needle or tubing.

Valve 80 includes a portion, such as, for example, a tip 86 and a portion, such as, for example, a body 88. Valve 80 includes a surface 100 that defines an axial passageway 102.

In some embodiments, passageway 102 may have cross section configurations, such as, for example, oval, cylindrical, triangular, square, polygonal, irregular, uniform, non-uniform, offset, staggered, undulating, arcuate, variable and/or tapered. Passageway 102 is in communication with passageways 22, 48, 64 to facilitate flow of fluid F into an expandable member.

Tip 86 includes an opening 87 configured to facilitate transfer of fluid F into an expandable member. Tip 86 is configured for disposal in passageway 48 and includes an outer surface 90. Upon disposal of tip 86 within passageway 48, surface 90 is spaced apart from surface 46 to define a clearance 92. Clearance 92 defines a portion of vent pathway 60, as described herein.

Body 88 includes an outer surface 94. In some embodiments, surface 94 includes a plurality of circumferential projections 96 configured for engagement with surface 62 to create a mechanical seal therewith. Engagement of projections 96 and surface 62 facilitates transfer of fluid F to an expandable member. Tip 86 extends from body 88 along a tapered surface 98.

In some embodiments, the connector 30/50 assembly is disposed with passageway 22 of cannula 14 and flange 38 engages surface 20 to create a mechanical seal therewith. Valve 80 is disposable with the connector 30/50 assembly and within passageways 48, 66. Valve 80 is assembled with connectors 30, 50 for axial translation between a vent position, as shown in FIG. 1, and a seal position, as shown in FIG. 2, under pressure of fluid F, as described herein.

In the vent position, surface 98 is spaced apart from surface 45 to define a clearance 99 therebetween and establish communication between clearance 92 and openings 74. In the vent position, vent pathway 60 is established and includes passageways 64, 102, 48, clearances 92, 99, openings 74 and clearance 58. In some embodiments, vent pathway 60 includes one or more passageways and/or openings (not shown) in communication with clearance 58 for expulsion and/or removal of vented air, gas, and/or fluids, and/or substances separated from surgical instrument 12 and/or fluid F.

For example, in the venting position, selected air, gas, and/or fluids, and/or substances can be disposed within the components of surgical instrument 12. As fluid F is supplied to an expandable member with surgical instrument 12 with source 55 of fluid F under pressure, in the direction shown by the indicated arrow in FIGS. 1 and 2, surgical instrument 12 removes the selected air, gas, and/or fluids, and/or substances from vent pathway 60 and/or fluid F. In some embodiments, the selected air, gas, and/or fluids, and/or substances has a lower viscosity than fluid F, such as, for example, silicone. As fluid F is supplied under pressure to an expandable member, the selected air, gas, and/or fluids, and/or substances having a lower viscosity is forced through vent pathway 60, in the direction shown by arrows A in FIG. 1, for expulsion and/or removal. Valve 80 remains in the vent position and the selected air, gas, and/or fluids, and/or substances travels along vent pathway 60 and about adjacent components of surgical instrument 12, as described herein.

As the selected air, gas, and/or fluids, and/or substances are released from vent pathway 60, the pressure and volume of the higher viscosity fluid F increases. The pressure of fluid F causes valve 80 to translate relative to connectors 30, 50, in the direction shown by arrow B in FIG. 2, to the sealed position. In the sealed position, surface 98 engages surface 45 to create a mechanical seal therewith. In the sealed position, a seal pathway 61, in the direction shown by arrows C in FIG. 2, is established and includes a source of fluid F, passageways 64, 102, 48, and a passageway of an expandable member. In the sealed position, seal pathway 61 facilitates transfer of fluid F to an expandable member for selective expansion thereof.

In some embodiments, flange 38 forms a fluid barrier to separate passageway 22 into a portion 40 and a portion 42, which comprise separate fluidic portions of passageway 22. In some embodiments, portion 40 includes passageways 48, 64, a passageway of an expandable member attached to end 32, and the section of passageway 22 disposed about connector 50 and/or a connection to a source of fluid F. In some embodiments, portion 42 includes the section of passageway 22 disposed about end 32 and/or outside of a connected expandable member. In some embodiments, end 32 is connected with an expandable member such that fluid F is restricted to conform within portion 40. In some embodiments, flange 38 engages surface 20 to separate vented air, gas, and/or fluids, and/or substances disposed outside of portion 40 from mixing with fluid F.

Figure 4:
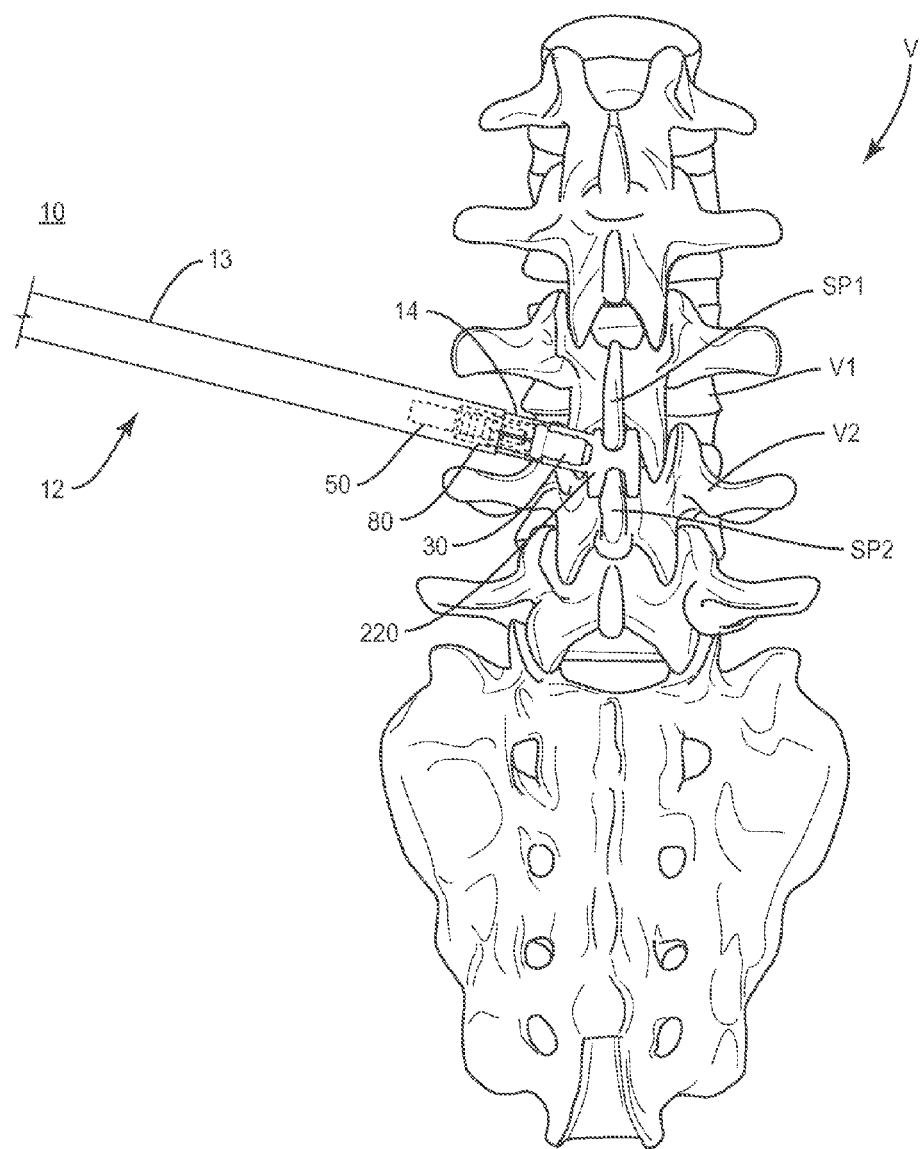
FIG. 4 is a perspective view of components of one embodiment of a surgical system in accordance with the principles of the present disclosure disposed with vertebrae.

In assembly, operation and use, surgical system 10 is employed to treat an affected section of a patient body, such as, for example, a lumber region of vertebrae V, as shown in FIG. 4. In some embodiments, a patient is in a prone position with the abdomen free and the spine slightly flexed to facilitate exposure of an inter-laminar space. A medical practitioner obtains access to a surgical site including vertebrae V in any appropriate manner, such as through incision and retraction of tissues.

Surgical system 10 may be used with surgical methods or techniques including open surgery, mini-open surgery, minimally invasive surgery and percutaneous surgical implantation, whereby vertebrae V is accessed through a mini-incision, or sleeve that provides a protected passageway to a surgical site.

Once access to the surgical site is obtained, a surgical treatment, for example, a spinal stabilization procedure can be performed for treating a spine disorder. A diseased and/or damaged portion of vertebrae V between and/or including vertebra V1, V2, and spinous processes SP1, SP2 can be removed. An interspinous space is prepared to a ligamentum flavum by dissection to remove interspinous ligament tissue and bony overgrowth to provide space for an interspinous implant 220. In some embodiments, tissue resectors are introduced into the interspinous space to free the muscular and ligamentous attachments of spinous processes SP1, SP2 and a lamina.

In some embodiments, the surgical treatment includes decompression. In some embodiments, a medial facetectomy, foraminotomy, and/or discectomy may be performed. Interspinous implant 220 maintains decompression while allowing motion of a treated vertebral segment. In some embodiments, interspinous implant 220 is selected after trialing based on preventing kyphosis and/or decreasing a risk of spinous process fracture.

The components of surgical system 10 including surgical instrument 12 are employed to augment the surgical treatment. Surgical instrument 12 can be delivered to a surgical site as a pre-assembled device or can be assembled in situ. Surgical system 10 may be may be completely or partially revised, removed or replaced.

In some embodiments, cannula 13 is introduced percutaneously to the surgical site to facilitate introduction and/or delivery of the components of surgical system 10. In some embodiments, connector end 32 is permanently attached in a fluid seal with interspinous implant 220 for implantation therewith. In some embodiments, connector end 32 is removably attached in a fluid seal with interspinous implant 220.

In some embodiments, interspinous implant 220 is attached with connector 30 in a non-expanded and/or deflated configuration, as shown in FIG. 4. The assembly of connectors 30, 50 is inserted and translated within passageway 22 such that surfaces 73 engage surface 20. End 54 mates with end 34 to interlock connectors 30, 50 in a fixed engagement within cannula 14, as described herein. Cannula 14 is delivered to the surgical site through cannula 13 to selectively position interspinous implant 220 between spinous process SP1 and spinous process SP2.

Source 55 of fluid F is attached with connector 50 to pressurize interspinous implant 220 with fluid F for expansion. Valve 80 is disposed in the venting position to vent air disposed within the components of surgical instrument 12. As fluid F is supplied to interspinous implant 220 with surgical instrument 12 with source 55 of fluid F under pressure, in the direction shown by the indicated arrow in FIGS. 1 and 2, surgical instrument 12 removes the air from vent pathway 60 and/or fluid F, as described herein. As fluid F is supplied under pressure to interspinous implant 220, the air having a lower viscosity than interspinous implant 220 is forced through vent pathway 60, in the direction shown by arrows A in FIG. 1, for expulsion and/or removal. Valve 80 remains in the vent position and the air travels along vent pathway 60 and about adjacent components of surgical instrument 12, as described herein.

As air is released from vent pathway 60, the pressure and volume of the higher viscosity fluid F increases. The pressure of fluid F causes valve 80 to translate relative to connectors 30, 50, in the direction shown by arrow B in FIG. 2, to the sealed position. In the sealed position, seal pathway 61 facilitates transfer of fluid F to interspinous implant 220 for selective expansion thereof. Flange 38 forms a fluid barrier to separate portions 40, 42, and separate the vented air, as well as gas, fluids and other substances disposed outside of portion 40 from mixing with fluid F. Fluid F is transferred to interspinous implant 220 to expand and/or inflate interspinous implant 220 at a selected cranial/caudal orientation between spinous process SP1 and spinous process SP2.

In some embodiments, surgical system 10 can include one or more surgical instruments for use with surgical instrument 12, such as, for example, drivers, inserters, extenders, reducers, spreaders, distracters, blades, retractors, clamps, forceps, elevators and drills, which may be alternately sized and dimensioned, and arranged as a kit.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae V. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of surgical system 10 are removed and the incision is closed. The components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical injection device comprising:
   a longitudinal element;
   a first member disposed with the longitudinal element and including a mating surface, the first member defining an axial passageway;
   a second member disposed with the longitudinal element and including a mating surface engageable with the mating surface of the first member and an inner surface defining an axial passageway; and
   a valve disposed within the passageways such that an outer surface of the valve engages the inner surface to create a mechanical seal therewith, the valve being axially translatable relative to the members between a vent position and a seal position.

2. A surgical injection device as recited in claim 1, wherein the valve is axially translatable via engagement with a pressurized fluid.

3. A surgical injection device as recited in claim 2, wherein in the vent position a gas is separable from the fluid through at least one opening of at least one of the members.

4. A surgical injection device as recited in claim 2, wherein in the seal position the fluid is transferred to an expandable member.

5. A surgical injection device as recited in claim 1, wherein the valve includes a tip disposed with the first member to define a clearance therebetween and a tapered surface extending from the tip.

6. A surgical injection device as recited in claim 5, wherein in the vent position the tapered surface is spaced from the first member and in the seal position the tapered surface engages the first member.

7. A surgical injection device as recited in claim 1, wherein the longitudinal element defines an axial passageway and the second member includes at least one lateral opening.

8. A surgical injection device as recited in claim 7, wherein the second member and the longitudinal element define a clearance therebetween, and the valve and the first member define a clearance therebetween.

9. A surgical injection device as recited in claim 8, further defining a vent pathway in the vent position, the vent pathway comprising the passageways, the clearances and the at least one lateral opening disposed in communication.

10. A surgical injection device as recited in claim 9, wherein the first member includes an outer surface that engages the longitudinal element to separate the passageway of the longitudinal element into a first portion and a second portion, the vent pathway including the second portion and being sealed from the first portion.

11. A surgical injection device as recited in claim 8, further defining a seal pathway in the seal position, the seal pathway comprising the passageways of the members and the valve disposed in communication.

12. A surgical injection device as recited in claim 1, wherein the mating surface of the first member includes a circumferential band and the mating surface of the second member includes a circumferential recess, the band being disposed with the recess to dispose the members in a fixed engagement.

13. A surgical injection device as recited in claim 1, wherein the second member includes a plurality of circumferentially disposed movable arms, the arms including the mating surface of the second member.

14. A surgical injection device as recited in claim 13, wherein the arms define at least one axial slot, each slot including a vent opening.

15. A surgical injection device comprising:
a cannula;
an implant connector including a seal engageable with the cannula and defining an axial passageway;
a vent connector lockable with the implant connector and including at least one lateral vent opening and an inner surface defining an axial passageway; and
a valve disposed within the passageways such that an outer surface of the valve engages the inner surface to create a mechanical seal therewith, the valve including a tip and a tapered surface extending from the tip, the valve being axially translatable between a vent position such that the tapered surface is spaced from the implant connector and a seal position such that the tapered surface engages the implant connector.

16. A surgical system comprising:
an injection device comprising a longitudinal element, a first member disposed with the longitudinal element and including an axial passageway and a mating surface, a second member disposed with the longitudinal element and including an inner surface defining an axial passageway and a mating surface engageable with the mating surface of the first member, and a valve within the passageways such that an outer surface of the valve engages the inner surface to create a mechanical seal therewith;
an expandable member connected with the first member; and
a pressurized fluid connected with the second member, wherein the valve is axially translatable via engagement with the fluid between a vent position such that a gas is separable from the fluid through at least one opening of at least one of the members and a seal position such that the fluid is transferred to the expandable member.

17. A surgical system as recited in claim 16, wherein the valve includes a tip disposed with the first member and a tapered surface extending from the tip, the valve being axially translatable between the vent position such that the tapered surface is spaced from the first member and the seal position such that the tapered surface engages the first member.

18. A surgical system as recited in claim 16, wherein the fluid includes silicone.

19. A surgical system as recited in claim 16, wherein the expandable member includes a spinal implant.

20. A surgical system as recited in claim 16, wherein the expandable member includes an inflatable balloon.

\* \* \* \* \*